United States Patent [19]

Lorenz et al.

[11] Patent Number: 5,318,599
[45] Date of Patent: * Jun. 7, 1994

[54] HAIR DYE COMPOSITION

[75] Inventors: Heribert Lorenz, Gross-Bieberau; Jürgen Tennigkeit, Seeheim-Jugenheim; Frank Kufner, Darmstadt, all of Fed. Rep. of Germany

[73] Assignee: Goldwell AG, Darmstadt, Fed. Rep. of Germany

[*] Notice: The portion of the term of this patent subsequent to Nov. 5, 2010 has been disclaimed.

[21] Appl. No.: 974,170

[22] Filed: Nov. 10, 1992

[30] Foreign Application Priority Data

Nov. 11, 1991 [DE] Fed. Rep. of Germany ............ 4136997.1-43

[51] Int. Cl.$^5$ .............................. A61K 7/13
[52] U.S. Cl. .................................. 8/405; 8/406; 8/407; 8/408; 8/416; 424/70
[58] Field of Search ............... 8/409, 408, 405, 406, 8/407, 414, 416, 423; 424/70

[56] References Cited

U.S. PATENT DOCUMENTS

| | | | |
|---|---|---|---|
| 4,129,414 | 12/1978 | Rose et al. | 8/409 |
| 4,226,595 | 10/1980 | Rose et al. | 8/408 |
| 4,322,212 | 3/1982 | Konrad et al. | 8/423 |
| 4,745,652 | 5/1988 | Rose et al. | 8/409 |
| 4,784,667 | 11/1988 | Maak et al. | 8/409 |
| 4,838,893 | 6/1989 | Rose et al. | 8/405 |
| 4,871,372 | 10/1989 | Mano et al. | 8/421 |
| 5,047,066 | 9/1991 | Mano et al. | 8/408 |
| 5,089,026 | 2/1992 | Tagami et al. | 8/408 |
| 5,104,414 | 4/1992 | Tamura et al. | 8/408 |
| 5,176,716 | 1/1993 | Lorenz et al. | 8/4 |

FOREIGN PATENT DOCUMENTS 3233540 3/1984 Fed. Rep. of Germany .
91058279 9/1991 Fed. Rep. of Germany .

*Primary Examiner*—Paul Lieberman
*Assistant Examiner*—Caroline L. Dusheck
*Attorney, Agent, or Firm*—Birch, Stewart, Kolasch & Birch

[57] ABSTRACT

Hair dye composition comprising at least one triaminohydroxypyrimidine and (or) diaminodihydroxypyrimidine as developing substance, and as coupling agent 3-amino-2-methylamino-6-methoxypyridine or salts thereof, on its own or in admixture with other coupling agents. Application of this composition in admixture with an oxidant onto human hair provides excellent natural-looking hair colorations.

7 Claims, No Drawings

HAIR DYE COMPOSITION

This invention refers to a new hair dye composition for human hair providing particularly improved dyeing properties, excellent toxicological properties and dermatological compatibility.

It is generally known in the art that hair dye compositions contain at least one oxidation dye precursor, a so-called developing substance, and coupling agents which are mixed with hydrogen peroxide immediately before application to the hair to provide the desired color reaction. Fine adjustment of a desired color shade is usually effected by the addition of shade modifiers.

Usual developing substances are particularly aromatic diamines such as p-phenylenediamine and p-toluylenediamine. For some users these substances are, however, not optimal with regard to their dermatological properties. For this reason there is a demand for further developing substances with improved dermatological and toxicological properties.

German Utility Model No.91 05 827.9 suggests for this purpose hair dye compositions containing as developing substance, on its own or in admixture with other developing substances, hydroxytriaminopyrimidines and (or) dihydroxydiaminopyrimidines, preferably 6-hydroxy 2,4,5-triaminopyrimidine, 2-hydroxy 4,5,6-triaminopyrimidine and 5-hydroxy 2,4,6-triaminopyrimidine or 2,6-dihydroxy-4,5-diaminopyrimidine and (or) 4,6-dihydroxy-2,5-diaminopyrimidine.

Preferred coupling agents for these developing substances are: Resorcinol, m-aminophenol, m-phenylenediamine, α-naphthol, p-amino-4-hydroxyethyl aminoanisole, o-aminophenol, o-chloro-p-phenylenediamine, 1,7-dihydroxynaphthalene and 3-dimethyl aminophenol, which usually give good dyeing results, but which are not always in optimal harmony with natural hair colors.

The present invention therefore starts from the problem of developing coupling agents which result in a natural hair coloration in combination with triaminohydroxypyrimidine and diaminodihydroxypyrimidine developing substances.

According to the invention this problem is solved by addition of 3-amino-2-methylamino-6-methoxypyridine as a coupling agent, alone or in admixture with other coupling agents, to the hair dye combination based on triaminohydroxy and (or) diaminohydroxy pyrimidine developing substances.

Due to the combination of these particular developing substances with the special coupling agents, hair colorings of outstanding natural appearance are obtained after the addition of hydrogen peroxide or other peroxides.

The use of 2,3-diamino-6-methoxypyridine derivatives as oxidation hair dye precursors, e.g., 3-amino-2-methylamino-6-methoxypyridine, is known from German Patent Application 3,233,540. However, in this publication these substances are exclusively used in combination with at least one aromatic diamine, 2-aminophenol and (or) 4-aminophenol to produce blue shades in particular.

It was therefore surprising and not foreseeable that, according to the invention, the combination of one of these pyridine derivatives, viz., 3-amino-2-methylamino-6-methoxypyridine, would lead to natural hair dye colorations with an entirely new class of developing substances, i.e., diaminohydroxy or triaminohydroxypyrimidines.

Preferred compounds mentioned in the preceding German Utility Model No. 9,105 827.9 are triaminohydroxypyrimidines or dihydroxydiaminopyrimidines which may also be used as salts, e.g. as hydrochloride, i.e. for example, 2,4,5-triamino-6-hydroxypyrimidine, 4,5,6-triamino-2-hydroxypyrimidine, 2,4,6-triamino-5-hydroxypyrimidine, 2,6-dihydroxy-4,5-diaminopyrimidine, and 4,6-dihydroxy-2,5-diaminopyrimidine.

Their proportion in the hair dye compositions according to the invention is from about 0.01 to 5, preferably from 0.1 to 4, particularly from 0.5 to 3% by weight of the total composition (excluding oxidant).

Although there is no essential need for them other known developing substances may optionally be added to produce certain color shades if desired, such as p-phenylenediamine, p-toluylenediamine, 4-aminophenol, and tetraaminopyrimidine or derivatives thereof.

According to the invention the coupling substance, i.e., 3-amino-2-methylamino-6-methoxypyridine, is present in the hair dye compositions in about the same proportion as the developing substances, i.e., in quantities from 0.05 to 5.0, preferably from 0.1 to 4, particularly from 0.5 to 3% by weight of the total composition (excluding oxidant).

Here again it is possible to add further known coupling agents if desired and necessary to achieve certain color shades.

If desired, the compositions according to the invention may also comprise so-called shade modifiers for fine adjustment of the shade, particularly so-called direct dyes. Those shade modifiers are, e.g., dyestuffs known under the name "Arianor", nitro dyes such as 2-amino-4,6-dinitrophenol, 2-amino-4-nitrophenol, 2-amino-6-chloro-4-nitrophenol, etc., preferably in quantities of about 0.05 to 2.5, preferably 0.1 to 1% by weight of the hair dye composition (excluding oxidants).

The hair dye compositions of this invention may contain any basic substances and additives, conditioning agents, etc. usual in those preparations, which are principally known to the expert and are included in technical literature, e.g., in the Monography of K. Schrader "Grundlagen und Rezepturen der Kosmetika", 2nd Edition (Hüthig Buch Verlag, Heidelberg, 1989), pp. 782 to 815. They may be prepared as lotions, creams, gels, or also aerosol compositions.

Before application to the hair, the oxidation dye precursor is blended with an oxidant. A preferred oxidant is hydrogen peroxide in a concentration of, e.g., 2 to 6%. However, other peroxides may also be used such as urea peroxide or melamine peroxide.

After admixture with peroxide, the pH value of the ready-to use hair dye composition may be weakly acidic, i.e. from pH 5.5 to 6.9, or neutral, or also alkaline, i.e. between pH 7.1 and 9.5.

A particularly mild hair dyeing process is achieved by application of a weakly acidic dye composition whereby the use of the coupling agent according to the invention provides especially natural looking hair shades.

The following examples illustrate the invention:

EXAMPLES

A

In a cream base of the following composition:

| | |
|---|---|
| Cetylstearylalcohol | 12.00% by wt. |
| Coconut fatty acid monoethanolamide | 2.00 |
| Ethoxylated stearic acid monoethanolamide (4 EO) | 0.80 |
| Oleic acid | 1.20 |
| Sodium hydroxide | 0.25 |
| Sodium lauryl sulfate | 0.50 |
| EDTA | 0.20 |
| Ammonium chloride | 0.20 |
| Sodium sulfite | 0.25 |
| Protein hydrolyzate | 1.00 |
| Manganese dioxide | 0.12 |
| Perfume | 0.20 |
| Water | @ 100.0, | the following oxidation dye precursors were included after an appropriate reduction of the water content:

No. 1:

| | |
|---|---|
| 2,5,6-Triamino-4-hydroxypyrimidine | 1.66% by wt. |
| 3-Amino-6-methoxy-2-methylaminopyrimidine | 1.56 |
| 2,6-Diaminopyridine | 1.24 |

No. 2:

| | |
|---|---|
| 2,5,6-Triamino-4-hydroxypyrimidine | 1.12% by wt. |
| 3-Amino-6-methoxy-2-methylaminopyridine | 1.04 |
| 2,6-Diaminopyridine | 0.14 |
| Picramic acid | 0.04 |

No. 3:

| | |
|---|---|
| 2,5,6-Triamino-4-hydroxypyrimidine | 0.90% by wt. |
| 3-Amino-6-methoxy-2-methylaminopyrimidine | 0.60 |
| Naphthalindiol-2,3 | 0.08 |
| 2-Methylresorcinol | 0.16 |
| 2,5-Diaminopyridine | 0.16 |
| Picramic acid | 0.04 |

No. 4:

| | |
|---|---|
| 2,5,6-Triamino-4-hydroxypyrimidine | 0.80% by wt. |
| 3-Amino-6-methoxy-2-methylaminopyrimidine | 0.20 |
| 2,5-Diaminopyridine | 0.55 |
| 2-Methylresorcinol | 0.10 |

No. 5:

| | |
|---|---|
| 2,5,6-Triamino-4-hydroxypyrimidine | 0.80% by wt. |
| 3-Amino-6-methoxy-2-methylaminopyrimidine | 0.11 |
| 2,5-Diaminopyridine | 0.40 |
| 2-Methylresorcinol | 0.30 |
| 2-Aminophenol | 0.10 |
| Picramic acid | 0.05 |

No. 6:

| | |
|---|---|
| 2,4-Dihydroxy-5,6-diaminopyrimidine | 0.76% by wt. |
| 3-Amino-6-methoxy-2-methylaminopyridine | 0.70 |

No. 7:

| | |
|---|---|
| 4,6-Dihydroxy-2,5-diaminopyrimidine | 0.75% by wt. |
| 3-Amino-6-methoxy-2-methylaminopyridine | 0.70 |

No. 8:

| | |
|---|---|
| 2-Hydroxy-4,5,6-triaminopyrimidine | 0.75% by wt. |
| 3-Amino-6-methoxy-2-methylaminopyridine | 0.70 |

20 grams each of these cream compositions were mixed with 40 ml of a 2% $H_2O_2$ solution which resulted in each case in a product with a pH value of 6.8 and which was applied onto human hair. After a processing time of 15 to 20 minutes the hair was washed and rinsed, and the following natural hair shades were obtained:

| | |
|---|---|
| No. 1: | dark brown |
| No. 2: | light brown |
| No. 3: | dark blonde |
| No. 4: | red beech |
| No. 5: | mahogany |
| No. 6: | pale golden blonde |
| No. 7: | hazel |
| No. 8: | ash-blonde |

B

In the following cream base composition:

| | |
|---|---|
| Cetylstearylalcohol | 12.00% by wt. |
| Coconut fatty acid monoethanolamide | 2.30 |
| Stearic acid monoethanolamide | 2.30 |
| Oleyalcohol ethoxylate (5 EO) | 0.50 |
| Oleic acid | 2.50 |
| 1,2-Propandiol | 2.00 |
| Sodium lauryl sulfate | 0.50 |
| EDTA | 0.20 |
| Ammonium chloride | 0.50 |
| Sodium sulfite | 0.50 |
| Ascorbic acid | 0.50 |
| Protein hydrolyzate | 1.00 |
| Ammonia, 25% | 7.20 |
| Perfume | 0.30 |
| Water | @ 100.00, | the following oxidation dye precursors were included after an appropriate reduction of the water content:

No. 1:

| | |
|---|---|
| 2,5,6-Triaminohydroxypyrimidine | 1.40% by wt. |
| 3-Amino-6-methoxy-2-methylaminopyridine | 0.47 |
| 3-Amino-2-hydroxypyridine | 1.17 |
| Naphthalindiol-1,7 | 0.56 |

No. 2:

| | |
|---|---|
| 2,5,6-Triamino-4-hydroxypyrimidine | 0.72% by wt. |
| 3-Amino-6-methoxy-2-methylaminopyridine | 0.65 |

No. 3:

| | |
|---|---|
| 4,6-Dihydroxy-2,5-diaminopyrimidine | 0.75% by wt. |
| 3-Amino-6-methoxy-2-methylaminopyridine | 0.70 |

20 g each of these cream compositions were mixed with 20 ml of a 6% $H_2O_2$ solution, each resulting in a pH 9.5 product which was applied onto human hair.

After 30 minutes processing time the hair was washed and rinsed. The following natural hair shades were achieved:

| | |
|---|---|
| No. 1: | intense fawn brown |
| No. 2: | intense ash-blonde |
| No. 3: | dark pale blonde |

What is claimed is:

1. A hair dye composition comprising a developing substance in an amount of from 0.01 to 5% by weight, based on the total composition, excluding oxidant, wherein said developing substance is selected from the group consisting of triaminohydroxypyrimidine, diaminodihydroxypyrimidine, and mixtures thereof, and at least one coupling agent in an amount of from 0.05 to 5.0% by weight, based on the total composition, excluding oxidant, wherein said coupling agent is selected from the group consisting of 3-amino-2-methylamino-6-methoxypyridine and water-soluble salts thereof.

2. The hair dye composition according to claim 1, further comprising additional coupling agents.

3. The hair dye composition according to claim 2, wherein said additional coupling agents are selected from the group consisting of resorcinol, m-aminophenol, m-phenylenediamine, α-naphthol, p-amino-4- hydroxyethyl amino anisole, o-aminophenol, o-chloro-p-phenylenediamine, 1,7-dihydroxynaphthalene, and 3-dimethylaminophenol.

4. The hair dye composition according to claim 1, further comprising at least one additional developing substance.

5. The hair dye composition according to claim 4, wherein said additional developing substance is selected from the group consisting of p-phenylenediamine, p-toluylenediamine, 4-aminophenol, and tetraaminopyrimidine.

6. The hair dye composition according to claim 1, wherein said 3-amino-2-methylamino-6-methoxypyridine coupling agent is present in an amount of 0.1 to 3% by weight, based on the total composition, excluding oxidant.

7. The hair dye composition according to claim 1 or 6, wherein mixing a said composition with peroxide results in a ready-to-use preparation having a pH between 5.5 and 6.9.

* * * * *